(12) United States Patent
Russell

(10) Patent No.: US 10,449,130 B2
(45) Date of Patent: *Oct. 22, 2019

(54) METHOD AND COMPOSITION FOR INHIBITING AGED SKIN

(71) Applicant: Kenneth O. Russell, Austin, TX (US)

(72) Inventor: Kenneth O. Russell, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/034,054

(22) Filed: Jul. 12, 2018

(65) Prior Publication Data

US 2018/0318184 A1 Nov. 8, 2018

Related U.S. Application Data

(63) Continuation-in-part of application No. 13/385,340, filed on Feb. 14, 2012.

(51) Int. Cl.
| | |
|---|---|
| *A61K 31/133* | (2006.01) |
| *A61K 33/06* | (2006.01) |
| *A61Q 19/08* | (2006.01) |
| *A61K 33/24* | (2019.01) |
| *A61K 31/51* | (2006.01) |
| *A61K 8/20* | (2006.01) |
| *A61K 8/23* | (2006.01) |
| *A61K 8/67* | (2006.01) |
| *A61K 8/41* | (2006.01) |
| *A61K 8/04* | (2006.01) |
| *A61K 9/00* | (2006.01) |
| *A61K 9/06* | (2006.01) |
| *A61K 8/49* | (2006.01) |

(52) U.S. Cl.
CPC ............... *A61K 8/20* (2013.01); *A61K 8/042* (2013.01); *A61K 8/23* (2013.01); *A61K 8/41* (2013.01); *A61K 8/49* (2013.01); *A61K 8/673* (2013.01); *A61K 9/0014* (2013.01); *A61K 9/0019* (2013.01); *A61K 9/06* (2013.01); *A61K 31/133* (2013.01); *A61K 31/51* (2013.01); *A61K 33/06* (2013.01); *A61K 33/24* (2013.01); *A61Q 19/08* (2013.01)

(58) Field of Classification Search
CPC ........ A61K 8/673; A61K 31/51; A61Q 19/00; A61Q 19/08; A61P 17/10
See application file for complete search history.

(56) References Cited

U.S. PATENT DOCUMENTS

| | | | | |
|---|---|---|---|---|
| 4,938,960 | A * | 7/1990 | Ismail | A61K 8/671 424/742 |
| 5,496,827 | A * | 3/1996 | Patrick | A61K 8/23 424/400 |
| 5,554,647 | A * | 9/1996 | Perricone | A61K 8/676 514/474 |
| 9,642,877 | B1 * | 5/2017 | Russell | A61K 33/24 |
| 2003/0190337 | A1 * | 10/2003 | Bissett | A61K 8/64 424/401 |
| 2004/0191206 | A1 * | 9/2004 | Cole | A61K 8/41 424/70.27 |
| 2006/0222689 | A1 * | 10/2006 | Lin | A61K 8/31 424/443 |
| 2006/0251608 | A1 * | 11/2006 | Wachsberg | A61K 8/02 424/74 |
| 2008/0057088 | A1 * | 3/2008 | Blass | A61K 8/0208 424/401 |

FOREIGN PATENT DOCUMENTS

| | | | |
|---|---|---|---|
| CA | 2637538 A1 * | 12/2009 | |
| EP | 1192940 A1 * | 4/2002 | ............ A61K 33/24 |
| JP | 2007153752 A * | 6/2007 | |

OTHER PUBLICATIONS

Grossman, Rachel. "The role of dimethylaminoethanol in cosmetic dermatology." American journal of clinical dermatology 6.1 (2005): 39-47.*

Clares, B., et al. "Structural characterization and stability of dimethylaminoethanol and dimethylaminoethanol bitartrate for possible use in cosmetic firming." Journal of cosmetic science 61.4 (2010): 269-278.*

* cited by examiner

*Primary Examiner* — Bethany P Barham
*Assistant Examiner* — Peter Anthopolos
(74) *Attorney, Agent, or Firm* — Pham IP Group; Frank H. Pham

(57) ABSTRACT

A method and composition for inhibiting aged skin by topically applying to human skin a topical anti-aging composition. The method involves applying the human skin of afflicted area with an effective amount of the anti-aging composition containing chromium chloride, thiamine mononitrate, magnesium sulfate, and dmae bitartrate for a period of time sufficient to impart the appearance of aged skin. The topical composition is formulated into a pharmaceutically acceptable medium to optimize glucose uptake into the skin cells to properly replace iron production of skin cells, thereby inhibiting the appearance of aged skin.

13 Claims, No Drawings

US 10,449,130 B2

METHOD AND COMPOSITION FOR INHIBITING AGED SKIN

CROSS-REFERENCE TO RELATED APPLICATION

The present application is based on, and claims the benefit of priority of, and U.S. patent application Ser. No. 13/385,340, filed Feb. 14, 2012. The entire content of each of these application and patents is hereby incorporated by reference.

BACKGROUND

1. Field of the Invention

The present invention relates generally to a topical skin anti-aging composition and a method for topically administering the skin anti-aging composition. More specifically, it relates to a method applying skin anti-aging composition in effecting transdermal delivery of chromium chloride, magnesium sulfate to the systemic circulation of a human body for treating, reducing, and preventing a superior anti-aging action. The composition is capable of being suitably used for cosmetic and topical pharmaceutical use.

2. Background of the Disclosure

The gradual development of facial wrinkles, whether fine surface lines or deeper creases and folds, is an early sign of accumulated skin damage and skin aging, which may be intrinsic and/or caused or accelerated by external factors. For example, premature aging and wrinkling of the skin may be accelerated by excessive exposure to the sun and other damaging elements, overactive facial expression muscles, frequent use of tobacco products, poor nutrition, or skin disorders.

Fine surface wrinkles that progress to deeper creases, deepening facial expression due to repeated skin folding, and deep folds which develop with one's maturity are visible changes which may combine to portray a less desirable appearance. Several invasive techniques are available in which substances are injected or implanted in the area of the skin which either temporarily weaken the muscles or act as skin volume fillers. However, invasive techniques are often risky and require the supervision or assistance of a physician, which can be inconvenient and costly, and non-invasive treatments have historically met with only minimal success. Regardless of the cause of facial creases or folds, safe and effective treatments for reduction or elimination of these problems have been exceedingly difficult to achieve.

The epidermis, the outermost layer of the skin, comprises a cellular continuum of four layers: the stratum corneum, the granular layer, the spinous layer, and the basal layer. Each cellular layer in the epidermis represents various stages along a process in which basal epidermal keratinocytes undergo a continuous cycle of proliferation, differentiation, and apoptosis, moving upward from the basal layer to finally yield corneocytes. These corneocytes form the cornified layer known as the stratum corneum.

Basal keratinocytes reside at the lower portion of the epidermis. These mitotically active cells undergo a proliferative cycle to generate daughter cells that are physically dislocated upward into the spinous and granular layers and undergo the process of differentiation into corneocytes. On passing through the spinous and granular layers, the cells undergo morphological changes that render them flatter in structure as they lose their cellular viability, undergo alternate keratin expression profiles, and transform into cellular remnants. On average, a younger-aged epidermis turns over in about one month, shedding the older cells and replacing them with newer ones, but this process can increase to over forty days in older skin.

Skin aging is a multifactorial process driven by both intrinsic (chronological aging) and extrinsic (environmental) factors, including ultraviolet (UV) exposure, environmental toxins, pollutants, and smoking. It is well known in the art that the ability of the stratum corneum to cyclically generate new layers of skin diminishes with age so that the stratum corneum turnover rate is substantially reduced in aged skin, with the cornified layer becoming gradually thinner.

This results in a reduction in the functioning capacity of the barrier so that harmful stimuli penetrate the stratum corneum more easily leading to UV-damage, for example, of the underlying dermal layers, degradation of collagen and elastin, and eventually manifests in appearance as wrinkling and skin atrophy. Thinning of the stratum corneum by the sum of intrinsic and extrinsic aging factors increases the visible appearance of fine lines and wrinkles.

Further, the barrier suffers from an age related increase in permeability to free radicals and a reduction in the amount of lipid in the intercellular matrix, decreasing barrier capacity to diffuse toxins from deeper layers.

Age-related skin changes are inevitable and include thinning, sagging, wrinkling, loss of elasticity, areas of dryness, and an inversed turnover of collagen type I/III ratio in the skin which presented as reduced synthesis of collagen type I but upregulated production of collagen type III. Currently, Mesotherapy has been arousing everyone's interest as an antiaging strategy. It is a minimally invasive procedure, which consists of intradermal micro injection of pharmacologic substances, such as nutrients, hormones, vitamins, enzymes, and other reagents, that have been diluted and are administered directly into the region to be treated. Under sterile and professional manipulation, Mesotherapy is very rarely causing troubles of skin infection and necrosis, except some minor risks like swelling and pain during the injection. Dimethyl amino ethanol (DMAE), an analog of the B vitamin choline and a precursor of acetylcholine, has been receiving more attention as an exciting new skincare supplement today for its acute effects of antiaging, anti-wrinkle, and skin firmness.

DMAE is well known for use in external application. In the randomized clinical studies, 3% DMAE facial gel has been shown to be safe and efficacious in the mitigation of forehead lines and periorbital fine wrinkles, and in improving lip fullness and shape and the overall appearance of facial skin. An open-label extension of the trial also showed that the long-term application of DMAE gel for up to 1 year was associated with a good safety profile. However, tropical treatment with DMAE usually requires high dose and concentration to pass through epidermal permeability bather, which could incur concerns of its toxicity, side effects, and medical costs. It was reported that 10 2.5-mml/mL DMAE could cause a vacuolar cytopathology of in vitro cultured human cells. In addition, studies showed that application of 3% DMAE gel tropically could also incur the vacuolar cytopathology of rabbit ear epidermal cells. Alternative delivery of DMAE is needed to evaluate the relative efficacy for the improvement of aging skin.

Type 2 diabetes mellitus (DM) is a disease characterized by dysfunction of various organs. Recent studies have shown a close relationship between DM and telomere attrition in leukocytes. In patients with DM or impaired glucose tolerance, excessive oxidative stress induces damage to telomeres and shortens their length. Furthermore, it is suggested that telomere length is a good surrogate marker for mortality and diabetic complications in DM patients. We recently found that telomere length in pancreatic β-cells is also shortened in DM patients, potentially leading to an impaired capacity for proliferation and insulin secretion, and accelerated skin cell death (https://accp1.onlinelibrary.wiley.com/doi/pdf/10.1002/jcph.113).

In an animal model, it has been shown that telomere attrition in adipose tissue induces insulin resistance. Taken together, the available data suggest that hyperglycemia, oxidative stress, and telomere attrition in pancreatic β-cells and adipocytes create a vicious cycle that underlies the pathophysiology of type 2 DM. Inhibition of telomere attrition in various organs, including pancreatic β-cells, could be a new approach for preventing the progression of DM and its complications (https://www.ncbi.nlm.nih.gov/pubmed/27018285).

Recovery capacity of the barrier to environmental insult is also substantially reduced with age. Thus, the skin's epidermal of aging signs such as fine lines and wrinkles. Accordingly, it would be desirable to provide compositions and methods of treatment with clinically insignificant side effects that can improve the skin's epidermal functioning and thus also improve the appearance of the aging skin.

Dermal collagen constitutes 90% of the dry way weight of skin. Loss of collagen is associated with normal aging process of human skin, the collagen rich extracellular matrix (ECM) is synthesized and maintained by dermal fibroblasts.

Transforming growth factor is crucial in ECM biosynthesis, and iron suppresses such transforming growth factor. In addition, iron also suppresses the insulin signaling for essential amino acid uptake for protein synthesis in the ECM.

Metformin in combination with chromium chloride and magnesium sulfate reduces the amount of iron loading in the skin. While metformin increase mitochondrial function in fibroblasts and collagen production, chromium chloride and magnesium sulfate composition reproduces the beneficial effects of metformin. The composition also increases protein synthesis for the restoration of aging collagen and skin maintenance.

The anti-aging preparation for external application to the skin and collagen cross-linking inhibitory preparation for external application to the skin according the present invention contain a chromium chloride and magnesium sulfate represented by shown formula. When incorporated into preparations for cutaneous application, the chromium chloride-magnesium sulfate exhibits inhibitory action on collagen cross-linking thereby making a great contribution to manifestation of the effects expected of the preparations.

That is, the collagen cross-linking inhibitory preparation of the present invention inhibits collagen cross-linking to make it possible to retain skin elasticity, prevent wrinkles or sagging and maintain a beautiful skin as far as collagen cross-linking is concerned.

Iron loading causes both diabetes pathologies, complications and telomere shrinkage (accelerated aging). Iron removal reverses these outcomes via antiaging. Iron loading via hemochromatosis increases transferrin saturation with iron and impairs the ability of chromium atoms to displace iron on the transferrin proteins to be loaded into cells. Iron suppresses chromium delivery into the cells, chromium reduces the rate of insulin mediated iron loading into the skin cells, and supplants iron in the insulin mediated uptake of transferrin bound iron skin cells.

Skin hydration is paramount to skin health and reduction of wrinkles. Transdermal chromium and magnesium enhance fluid up take and retention into cells, enhance amino acid uptake for protein synthesis for more collagen and anti-oxidants, enhance sebum preservation from peroxidation by ultraviolet radiation. Sebum preservation restores water retention, and youthful appearance and younger skin texture.

Magnesium delivery increases cellular uptake of potassium and therefore restores normal fluid content of skin cells. All cells dehydrate without adequate potassium uptake. Magnesium optimizes microvascular vasodilation and optimized delivery of nutrients from the capillary blood to the skin cells. This could be characterized as optimized inside out nutrition of the skin cells. Increased amino acid delivery from capillary blood and increased amino acid uptake into skin cells (mediated by chromium and insulin) combine to increase protein synthesis for increased collagen, and iron regulatory proteins, and endogenous antioxidants. Increased collagen restores skin flexibility, skin texture, and reduces wrinkles. Increased ceruloplasmin (an iron regulatory protein) mediates the increased efflux of intracellular iron from skin cells via the ferroportin receptor. Transdermal chromium displaces iron atoms on the transferrin protein prior to uptake into skin cells. This reduces inflammatory iron content of skin cells.

SUMMARY OF THE INVENTION

The present invention relates to a safe and efficient composition comprising chromium chloride in combination with magnesium sulfate, thiamine mononitrate, and dmae bitartrate in effective amounts and a member selected from the group of physiologically chemical groups consisting of mineral oil, glyceryl stearate, and propylene glycol in association with a topical pharmaceutical carrier for solutions, suspensions, ointments, lotions, creams gels, pastes, jellies, sprays, and aerosols and/or together with a medical device.

The present invention provides a skin anti-aging composition that contains a non-toxic additive acting as a skin penetration enhancer. The chromium complexes may contain chromium in the (III) (i.e., trivalent), or other valent states, although it is believed that the trivalent state is responsible for biological effects of interest in the present invention and is therefore preferred. Chromium in many of the chromium containing complexes contemplated by the present invention typically have chromium in the (III) equivalency.

Alternatively, as discussed for other components, the appropriate dose of magnesium sulfate may be based on the condition of any subject.

Alternatively, the dosages may depend on the mode of administration of the composition.

Alternatively, magnesium sulfate may vary with the identity and amounts of the other components in any supplement of the present invention. As for the other components of the subject compositions, appropriate dosages may depend on numerous factors, and may be readily determined by one of skill in the art.

The composition further contains a pharmaceutically acceptable carrier or excipient of magnesium sulfate as a multiplier to accelerate the effective transdermal delivery of chromium chloride. The magnesium component increases the distribution of chromium through the enlarged microvessels and into the skin cells.

The composition is topically administered to the human skin in a form of lotion, in a fixed-dose of combination, comprising chromium chloride and magnesium sulfate formulated as a topical composition to a patient in need, wherein the administration pattern of the composition comprises administering a therapeutically effective amount of the composition for at least 1 week, preferably for at least 2 weeks, more preferred for at least 4 weeks.

The composition is topically administered daily and preferably twice a day. In another embodiment, the composition is topically administered every two days and preferably once a day. In both cases, the composition is preferably administered in the evening after wash.

The composition according to the invention can be formulated in a variety of forms for topical application and comprises at least 0.000422% of chromium chloride by weight and preferentially comprises from about 0.00127% to about 0.00169% by weight of chromium chloride relative to the total weight of the composition. Within the preferred range, the composition comprises from about 0.676% to about 2.705% by weight of magnesium sulfate, preferably comprises 2.028% to 2.705% by weight of magnesium sulfate relative to the total weight of the composition. The composition further comprises from about 0.676281% to about 2.028843% by weight of thiamine and from about 2.113378% to about 6.340136% by weight of dmae bitartrate.

The compositions can include a cosmetically acceptable vehicle. Such vehicle may take the form of any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing The vehicle may comprise an aqueous phase, an oil phase an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The administration of a composition comprising chromium chloride and magnesium sulfate to a human subject sustains its biological response in the treatment of aged skin, wherein the administration pattern of the composition comprises topically applying to the human skin chromium chloride and magnesium sulfate twice daily for at least 1 week, preferentially for at least 2 weeks, more preferred for at least 4 weeks.

The term "topical administration" means topical application, transdermal application, or any combination thereof.

The term "pharmaceutically acceptable medium" means a medium that is compatible with the skin, mucous membranes and the integuments.

The term "fixed combination" should be understood as meaning a combination whose active principles are combined at fixed doses in the same vehicle/medium (single formula) that delivers them together to the point of application. Preferably, the pharmaceutical composition in the form of a fixed combination is lotion. In this case, the two active principles are dispersed and intimately mixed, during the manufacture, in the same vehicle, which delivers them together during the application of the lotion.

An embodiment of the present invention further provides vehicles and vehicle components that are especially useful in the transdermal formulations, as well as concentration ranges and processing steps to obtain useful formulation forms including solids, creams, lotions, gels, and liquids.

The present invention further provides objects and advantages that will become apparent from a description of the several embodiments as set forth in the following description.

DETAILED DESCRIPTION OF THE INVENTION

The present invention features a method for the treatment of aged skin by the topical administration of anti-aging skin composition to optimize glucose uptake into the skin cells to properly replace iron production of skin cells, thereby inhibiting the appearance of aged skin.

The composition disclosed in the present invention contains chromium chloride, magnesium sulfate, thiamine mononitrate, and dmae bitartrate. The following details a study that clearly demonstrates the clinical benefit of the composition.

The amount of chromium chloride which may be used in the present invention ranges from about 0.000422 to 0.00169 percent by weight and preferably about 0.676 to 2.705 percent by weight of magnesium sulfate of the composition.

Chromium chloride, magnesium sulfate, thiamine mononitrate, and dmae bitartrate are available commercially and are made by a number of methods known to those of skill in the art.

The composition can be incorporated into solution, lotion, cream, ointment and gel formulations for application to the aged skin of a subject. In such topical formulations, concentrations from 0.000422% to 0.00169% by weight of chromium chloride and 0.676% to 2.705% by weight of magnesium sulfate are incorporated into vehicle suitable for application to the skin. The resulting formulations are applied to the subject's aged skin from 1 to 2 times daily.

EXAMPLE 1

A clinical study of human subjects with aged skin was carried out to show the effectiveness of the anti-aging skin composition of the present invention. A fixed dose combination of lotion formulations containing chromium chloride 0.000422% to 0.001695% by weight/total composition weight.

Compositions containing 0.5 mg by weight of chromium chloride are topically administered at least once daily for 1 week to the human subjects with aged skin. At the end of one week period most subjects will demonstrate a significant decrease in the activity of their aged skin. Formulations A, B, C, D, and E (Table 1) were applied to each subject twice daily. Clinical appraisal was carried out at weekly intervals.

TABLE 1

| Components | Weight (%) | | | | |
|---|---|---|---|---|---|
| | A | B | C | D | E |
| Chromium chloride | 0.000422 | 0.000844 | 0.00127 | 0.00152 | 0.00169 |
| Magnesium sulfate | — | 0.676 | 2.028 | 2.608 | 2.705 |
| Thiamine mononitrate | — | 0.676281 | 1.05876 | 2.008209 | 2.028843 |
| Dmae bitartrate | — | — | 2.113378 | 5.809252 | 6.340136 |
| Total | 100 | 100 | 100 | 100 | 100 |

The results of the study are shown in Table 2 below:

TABLE 2

Clinical Evaluation of Treatment

| Formulation | Evaluation Time (Weeks) | | | |
|---|---|---|---|---|
| | 1 | 2 | 3 | 4 |
| A | 0 | 1 | 1 | 1 |
| B | 1 | 2 | 3 | 3 |
| C | 2 | 3 | 3 | 3 |
| D | 3 | 3 | 4 | 4 |
| E | 2 | 3 | 3 | 4 |

0 = no response
1 = slight improvement
2 = good improvement
3 = very good improvement
4 = dramatic improvement The results of the foregoing tests show that chromium chloride used in the systemic treatment of aged skin (formulation A) is essentially ineffective as is the vehicle alone. However, the results of the foregoing tests shown a good improvement with magnesium sulfate, thiamine mononitrate, and dmae bitartrate (formulation C, D, and E).

EXAMPLE 2

The study of Example 1 is repeated to show the efficacy of the anti-aging composition of the present invention (Table 3). The efficacy variables were subject's assessment of appearance of aged skin on a scale from 1 (marked improvement) to 5 (worse).

TABLE 3

| 1 | Marked Improvement |
| 2 | Moderated Improvement |
| 3 | Minimal Improvement |
| 4 | No Change |
| 5 | Worse |

Local tolerability measures of the signs and symptoms of skin irritation were considered adverse effects only if the severity of the expected signs and symptoms was such that an interruption of the subject's participation in the study, at his/her request or at the investigator's discretion, had occurred. Altered dosing regimens (such as every other day dosing) to manage irritation were not considered to be an interruption of the subject's participation in the study (Table 4).

Safety and tolerability were assessed through evaluations of local tolerability and adverse events. At each visit, the investigator rated erythema, scaling, dryness, stinging/burning on a scale.

TABLE 4

| 1 | No reaction |
| 2 | Minimal reaction |
| 3 | Moderated reaction |
| 4 | Extreme reaction |

The results of the safety and tolerability study are shown in Table 5 below.

TABLE 5

Efficacy and Safety Measurements

Efficacy

| Formulation | Evaluation Time (Weeks) | | | |
|---|---|---|---|---|
| | 1 | 2 | 3 | 4 |
| A | 4 | 4 | 3 | 3 |
| B | 4 | 3 | 3 | 3 |
| C | 3 | 3 | 2 | 2 |
| D | 2 | 1 | 1 | 1 |
| E | 3 | 2 | 1 | 1 |

Safety and Tolerability

| Formulation | Evaluation Time (Weeks) | | | |
|---|---|---|---|---|
| | 1 | 2 | 3 | 4 |
| A | 3 | 3 | 3 | 3 |
| B | 3 | 2 | 2 | 2 |
| C | 2 | 2 | 2 | 2 |
| D | 1 | 1 | 1 | 1 |
| E | 2 | 1 | 1 | 1 |

As this was an open-label study, only descriptive data presentations were made. No formal statistical hypotheses were tested. Descriptive statistics were used to summarize all data.

Treatment with chromium chloride 0.00152 for up to 3 weeks showed remarkably continuing improvement in imparting aged skin. The greatest imparts of aged skin were seen after 3 weeks.

Overall improvement was observed in the subject's assessment of appearance of aged skin. The median assessment was "Moderated Improvement" at week 2, and "Marked Improvement" at week 3.

In conclusion, chromium chloride 0.00152% and magnesium sulfate 2.608% were well-tolerated and effective in anti-aging skin. Signs and symptoms of skin irritation (erythma, dryness, scaling, and stinging/burning) were mostly minimal or moderate and were transient.

Safety findings were consistent with the known profile of chromium chloride. No unexpected, either systemic or dermatological, evidence of cumulative toxicity was observed over time. Consequently, extending treatment beyond 6 weeks does not suggest substantial additional risk for the subjects treated with chromium chloride 0.00152%.

The efficacy of chromium chloride 0.00152% and magnesium sulfate 2.608% was showed continuing improvement greater than 95% for subjects treated for 4 weeks.

As various modification could be made to the exemplary embodiments, as described above with reference to the corresponding illustrations, without departing from the scope of the invention, it is intended that all matter contained in the foregoing description and shown in the accompanying examples shall be interpreted as illustrative rather than limiting. Thus, the breadth and scope of the present invention should not be limited by any of the above described exemplary embodiments, but should be defined only in accordance with the following claims appended hereto and their equivalents.

Having illustrated and described the principles of the present invention in a preferred embodiment, it will be apparent to those skilled in the art that the embodiment can be modified in arrangement and detail without departing from such principles. Any and all such embodiments are intended to be included within the scope of the following claims.

What is claimed is:

1. A method of inhibiting skin aging in a human comprising topically applying, to an area of the human's skin, a composition comprising:
   (i) about 0.000422% to about 0.00169% by weight of chromium (III) chloride;
   (ii) about 0.676% to about 2.705% by weight of magnesium sulfate;
   (iii) about 0.676281% to about 2.028843% by weight of thiamine mononitrate;
   (iv) about 2.113378% to about 6.340136% by weight of dimethylaminoethanol (DMAE) bitartrate; and
   (v) a cosmetically-acceptable vehicle.

2. The method of claim 1, wherein the composition is in the form of a solution, a suspension, an ointment, a lotion, a cream, a gel, a spray, or an aerosol.

3. The method of claim 1, wherein the composition is in the form of an emulsion selected from the group consisting of water-in-oil emulsion, oil-in-water emulsion, silicone-in-water emulsion, water-in-silicone emulsion, wax-in-water emulsion, and water-oil-water triple emulsion.

4. The method of claim 1, wherein the composition further comprises an antioxidant.

5. The method of claim 1, wherein the composition further comprises a mineral oil.

6. The method of claim 1, wherein the composition further comprises glyceryl stearate.

7. The method of claim 1, wherein the composition further comprises propylene glycol.

8. The method of claim 1, wherein the cosmetically-acceptable vehicle is selected from the group consisting of water, a vegetable oil, an ester, an ether, an alcohol, a fatty alcohol, an isoparaffin, a silicone oil, a hydrocarbon oil, a polyol, a wax, and mixtures thereof.

9. The method of claim 1, wherein the cosmetically-acceptable vehicle is selected from the group consisting of water, deionized water, octyl palmitate, isopropyl myristate, isopropyl palmitate, dicapryl ether, dimethyl isosorbide, ethanol, isopropanol, cetyl alcohol, cetearyl alcohol, stearyl alcohol, biphenyl alcohol, isooctane, isododecane, hexadecane, cyclomethicone, dimethicone, dimethicone crosspolymer, a polysiloxane, an organo-modified polysiloxane, mineral oil, petrolatum, isoeicosane, polyisobutene, propylene glycol, glycerin, butylene glycol, pentylene glycol, hexylene glycol, a beeswax, a botanical wax, and mixtures thereof.

10. The method of claim 1, wherein the area of the human's skin is wrinkled.

11. The method of claim 1, wherein the composition is topically applied to the area of the human's skin at least once daily for at least one week.

12. The method of claim 11, wherein the composition is topically applied to the area of the human's skin twice daily.

13. The method of claim 1, wherein following the step of topical application, the chromium (III) chloride reduces the rate of insulin-mediated iron loading into cells of the human's skin.

* * * * *